(12) United States Patent
Sawanoi et al.

(10) Patent No.: US 8,764,670 B2
(45) Date of Patent: Jul. 1, 2014

(54) BLOOD PRESSURE INFORMATION MEASUREMENT DEVICE

(75) Inventors: Yukiya Sawanoi, Nara (JP); Yoshihide Tokko, Kyoto (JP)

(73) Assignee: Omron Healthcare Co., Ltd., Kyoto (JP)

(*) Notice: Subject to any disclaimer, the term of this patent is extended or adjusted under 35 U.S.C. 154(b) by 555 days.

(21) Appl. No.: 13/100,739

(22) Filed: May 4, 2011

(65) Prior Publication Data

US 2011/0208070 A1    Aug. 25, 2011

Related U.S. Application Data

(63) Continuation of application No. PCT/JP2009/068125, filed on Oct. 21, 2009.

(30) Foreign Application Priority Data

Nov. 4, 2008  (JP) .................................. 2008-283338

(51) Int. Cl.
*A61B 5/02*    (2006.01)

(52) U.S. Cl.
USPC .......................................................... 600/490

(58) Field of Classification Search
USPC .................................. 600/485, 490, 493, 494
See application file for complete search history.

(56) References Cited

U.S. PATENT DOCUMENTS 6,120,459 A * 9/2000 Nitzan et al. .................. 600/493

FOREIGN PATENT DOCUMENTS

| EP | 2 047 795 A1 | 4/2009 |
| JP | 54-050175 A | 4/1979 |
| JP | 54-050176 A | 4/1979 |
| JP | 10-137204 A | 5/1998 |
| WO | 2008/015921 A1 | 2/2008 |

OTHER PUBLICATIONS

International Search Report issued in PCT/JP2009/068125 mailed on Nov. 17, 2009, and English translation thereof, 2 pages.
Patent Abstracts of Japan, Publication No. 10-137204, Publication Date: May 26, 1998, 1 page.

* cited by examiner

*Primary Examiner* — Navin Natnithithadha
*Assistant Examiner* — Etsub Berhanu
(74) *Attorney, Agent, or Firm* — Osha • Liang LLP

(57) ABSTRACT

During a period of servo control, an artery volume of a peripheral site is detected by an artery volume sensor arranged at a peripheral site (site on the peripheral side than a measurement site) of a person to be measured. If an amount of change in the artery volume of the peripheral site or a value of the artery volume is greater than or equal to a predetermined ratio of a reference value at the beginning of the measurement, the servo control and a blood pressure determination process are continued. When detected thereafter that the amount of change in the artery volume of the peripheral site or the value of the artery volume is smaller than the predetermined ratio of the reference value at the beginning of the measurement, the measurement is stopped at the relevant time point.

12 Claims, 16 Drawing Sheets

(A)

(B)

BLOOD PRESSURE INFORMATION MEASUREMENT DEVICE

TECHNICAL FIELD

The present invention relates to blood pressure information measurement devices, and in particular, to a blood pressure information measurement device capable of measuring blood pressure information using a volume compensation method.

BACKGROUND ART

A blood pressure is one index for analyzing a cardiovascular disease. Performing risk analysis of the cardiovascular disease based on the blood pressure is effective in preventing cardiovascular diseases such as apoplexy, cardiac arrest, cardiac infarct and the like. Among them, an early morning high blood pressure, in which the blood pressure rises early in the morning is related to heart disease, apoplexy, and the like. Furthermore, a symptom of the early morning high blood pressure called the morning surge in which the blood pressure suddenly rises between one hour and one and a half hour after waking up is known to have a causal connection with apoplexy.

Therefore, it is useful in the risk analysis of the cardiovascular disease to grasp a mutual relationship of time (lifestyle habit) and change in blood pressure. The blood pressure thus needs to be continuously measured over a long period of time.

When monitoring a patient during surgery and after surgery, or when checking an effect of medicine at the time of antihypertensive treatment, and the like, it is very important to measure the blood pressure continuously for every heart beat, and to monitor the change in blood pressure. A blood pressure waveform for every heart beat contains information that is of a very wide medical usage range such as advancement in arterial sclerosis, and diagnosis of heart function. It is thus also important to continuously record the fluctuation of the blood pressure waveform.

Japanese Unexamined Patent Publication No. 54-50175 (Patent Document 1) describes a sphygmomanometer that uses a volume compensation method as a technique for measuring the blood pressure for every heart beat. The volume compensation method is as follows. An artery is compressed by a cuff from outside a living body, and a volume (volume per unit length) of the artery that pulsates in synchronization with the heart beat is maintained constant on a steady basis. The pressure (cuff pressure) at which a measurement site is compressed and an inner pressure, that is, the blood pressure of the artery or the measurement site are made equilibrium by maintaining the volume of the artery constant. The cuff pressure when this equilibrium state is maintained is detected to continuously obtain the blood pressure value.

Patent Document 1: Japanese Unexamined Patent Publication No. 54-50175

SUMMARY OF INVENTION

In the volume compensation method, the volume of the artery when the cuff pressure and the inner pressure of the artery are in the equilibrium state, that is, when the artery wall is in the no-load state, is detected as a target value of the servo control (hereinafter referred to as "control target value"). The cuff pressure is then controlled so that the artery volume that changes by the pulsation of every heart beat matches the control target value (servo control).

The measurement site is constantly compressed at the cuff pressure of higher than or equal to the diastolic blood pressure during the period of servo control. Thus, the vein in which the inner pressure of the blood vessel is lower than the diastolic blood pressure is constantly closed by pressure (compressed and crushed). Therefore, the reflux of the blood sent to the peripheral side than the measurement site back to the heart is inhibited. As a result, the blood retains at the peripheral side of the measurement site as the time elapses (congestive state).

When congestion occurs, the blood pressure cannot be correctly measured. If the congestive state continues for a long time, the tissues on the peripheral side may degenerate or necrotize. Thus, it is very important from the standpoint of accurate blood pressure measurement and ensuring safety of the person being measured to prevent congestion.

However, in a conventional sphygmomanometer (blood pressure information measurement device) of the volume compensation method, the congestion is not particularly monitored.

Therefore, one or more embodiments of the present invention provides a blood pressure information measurement device capable of monitoring the congestive state on the peripheral side of the measurement site.

A blood pressure information measurement device according to one or more embodiments of the present invention is a blood pressure information measurement device for measuring blood pressure information according to a volume compensation method, the blood pressure information measurement device including a cuff to be wrapped around a predetermined site; a pressure detection unit for detecting a cuff pressure representing a pressure in the cuff; a first volume detection unit, arranged at a predetermined position of the cuff, for detecting a volume of a first artery at the measurement site; a second volume detection unit for detecting a volume of a second artery at a peripheral site, which is a site on a peripheral side than the measurement site; a detection processing unit for performing a process for detecting a target value of a servo control; a servo control unit for carrying out the servo control so that a difference between the volume of the first artery and the target value of the servo control is smaller than or equal to a predetermined value; a blood pressure determination unit for determining the cuff pressure when an amplitude in change in volume of the first artery is smaller than or equal to the predetermined value as a blood pressure according to the servo control; and a congestion detection unit for detecting congestion of the peripheral site based on an output from the second volume detection unit during a period of servo control.

According to one or more embodiments of the present invention, the congestion detection unit detects congestion by detecting a temporal change for the volume of the second artery from beginning of the measurement.

According to one or more embodiments of the present invention, the congestion detection unit detects congestion from a ratio or a difference of a current amount of change in the volume of the second artery and an amount of change in the volume of the second artery at the beginning of the measurement.

Alternatively, the congestion detection unit detects congestion from a ratio or a difference of a current volume value of the second artery and a volume value of the second artery at the beginning of the measurement.

According to one or more embodiments of the present invention, the beginning of the measurement represents a time point at which the amplitude in the change in volume of the first artery becomes smaller than or equal to the predetermined value for a first time since the servo control started.

Alternatively, the beginning of the measurement represents a time point at which the target value of the servo control is detected.

Alternatively, the beginning of the measurement represents a time point before a start of a process of the detection processing unit.

According to one or more embodiments of the present invention, a stop processing portion for performing a process of stopping the measurement when congestion is detected by the congestion detection unit is further arranged.

According to one or more embodiments of the present invention, a notification processing portion for performing a process of notifying congestion information when congestion is detected by the congestion detection unit is further arranged.

According to one or more embodiments of the present invention, the notification processing portion notifies the detection of the congestion as the congestion information.

Alternatively, the congestion detection unit further determines a congestion level; and the notification processing portion notifies the congestion level as the congestion information.

Alternatively, a storage unit for storing the blood pressure information corresponding to a determination result by the blood pressure determination unit; and a recording processing portion for performing a process of recording presence of detection of congestion by the congestion detection unit in the storage unit in association with the blood pressure information are further arranged.

According to one or more embodiments of the present invention, the presence of congestion at the peripheral site can be detected during the period of servo control. Furthermore, one of the process for stopping the measurement and the process for outputting the congestion information is carried out based on the detection result of the congestion, and hence, only the blood pressure information of high reliability is presented to a doctor or the like.

DETAILED DESCRIPTION OF INVENTION

Figure 1:
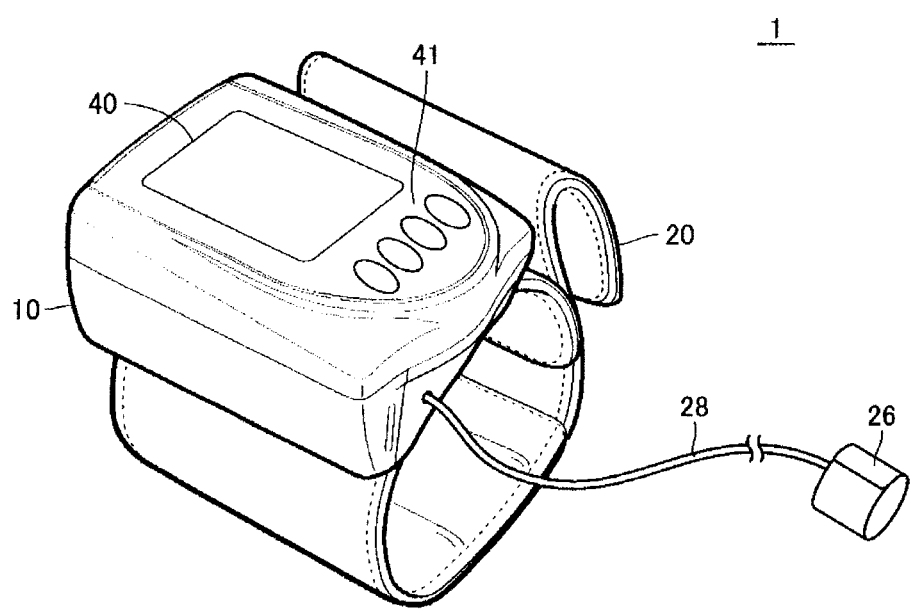
FIG. 1 is a perspective view of an outer appearance of a blood pressure information measurement device according to a first embodiment of the present invention.

Embodiments of the present invention will be described in detail with reference to the drawings. The same reference numerals are denoted for the same or corresponding portions in the figures, and the description thereof will not be repeated.

[First Embodiment]

A blood pressure information measurement device in a first embodiment of the present invention measures blood pressure information based on a volume compensation method. In the present embodiment, the "blood pressure information" is the information indicating characteristics of a circulatory system, and includes at least a pulse wave (pulse wave signal), and also includes an index that can be calculated from the pulse wave in addition to the pulse wave such as a continuous blood pressure value (blood pressure waveform), systolic blood pressure, diastolic blood pressure, average blood pressure, pulse rate, and AI (Augmentation Index) value.

The pulse wave, which is one type of blood pressure information, includes a pressure pulse wave and a volume pulse wave due to the difference in the target to capture. The pressure pulse wave captures the pulse wave as fluctuation of the cuff pressure involved in the volume change of the cuff by converting the fluctuation in the volume in the blood vessel involved in the pulsation of the heart to the volume change of the cuff, and can be obtained based on the output from the pressure sensor. The volume pulse wave captures the pulse wave as fluctuation of the volume in the blood vessel involved in the pulsation of the heart, and can be obtained based on the output from the artery volume sensor. The fluctuation of the volume in the blood vessel can be captured as the fluctuation in the blood tissue amount in the blood vessel.

The term "blood pressure information measurement device" as used herein refers to a general device having at least the function of acquiring the pulse wave, and more specifically, refers to a device for detecting the fluctuation in the blood tissue amount through an optical method to acquire the volume pulse wave to comply with the volume compensation method. In this regard, it is not limited to a device for outputting the acquired volume pulse wave as a measurement result, and may be a device for outputting only a specific index calculated or measured based on the acquired volume pulse wave as the measurement result, or a device for outputting both the volume pulse wave and the specific index as the measurement result.

The blood pressure information measurement device according to the first embodiment of the present invention described below acquires the blood pressure waveform by continuously measuring the blood pressure through the volume compensation method.

<Regarding Outer Appearance and Configuration>

(Regarding Outer Appearance)

FIG. 1 is a perspective view of an outer appearance of a blood pressure information measurement device 1 according to a first embodiment of the present invention. The outer appearance of the blood pressure information measurement device 1 is similar to a general sphygmomanometer.

With reference to FIG. 1, the blood pressure information measurement device 1 includes a main body 10, a cuff 20 that can be wrapped around a predetermined measurement site such as the wrist and a peripheral unit 26 for attaching to a body site (hereinafter referred to as "peripheral site") on the peripheral side than the measurement site. The peripheral unit 26 is electrically connected to the main body 10 by a cord 28.

The main body 10 is attached to the cuff 20. A display unit 40 configured by a liquid crystal and the like, and an operation unit 41 for accepting instructions from a user (representatively, person to be measured) are arranged on the surface of the main body 10. The operation unit 41 includes a plurality of switches.

In the present embodiment, the description will be made assuming that the measurement site is the wrist. However, the measurement site is not limited to the wrist and may be the upper arm.

Figure 2:
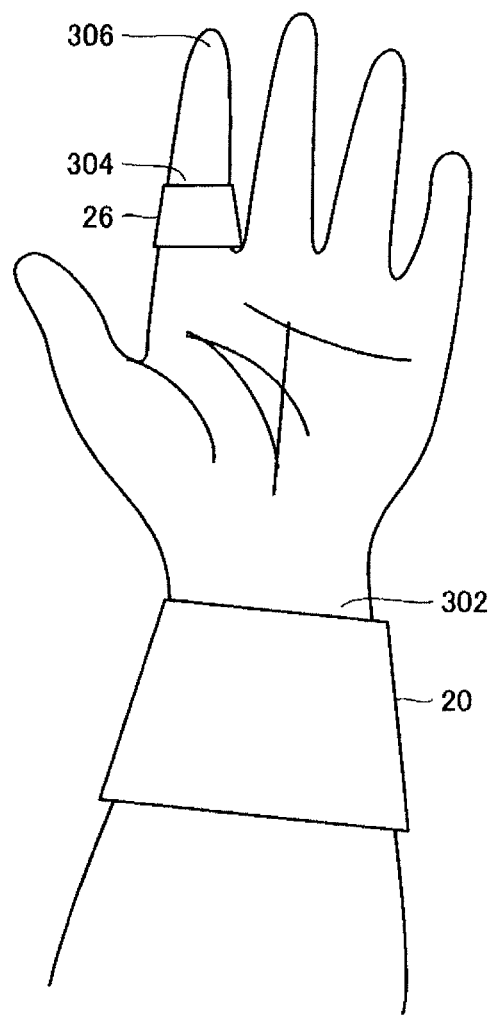
FIG. 2 is a view showing the relationship of a measurement site and a peripheral site.

FIG. 2 is a view showing the relationship of the measurement site and the peripheral site.

With reference to FIG. 2, the site (peripheral site) where the peripheral unit 26 is attached when the measurement site where the cuff 20 is attached is the wrist 302 is a finger base portion (base portion of the finger) 304. Such a site is not restricted as long as it is on the peripheral side than the measurement site and may be a tip of the finger 306.

The blood pressure information measurement device 1 according to the present embodiment will be described using a mode in which the main body 10 is attached to the cuff 20 as an example, as shown in FIG. 1. However, a mode in which the main body 10 and the cuff 20, which are separated, are connected with an air tube (air tube 31 in FIG. 2) as adopted in the upper arm type blood pressure information measurement device may be used.

(Regarding Hardware Configuration)

Figure 3:
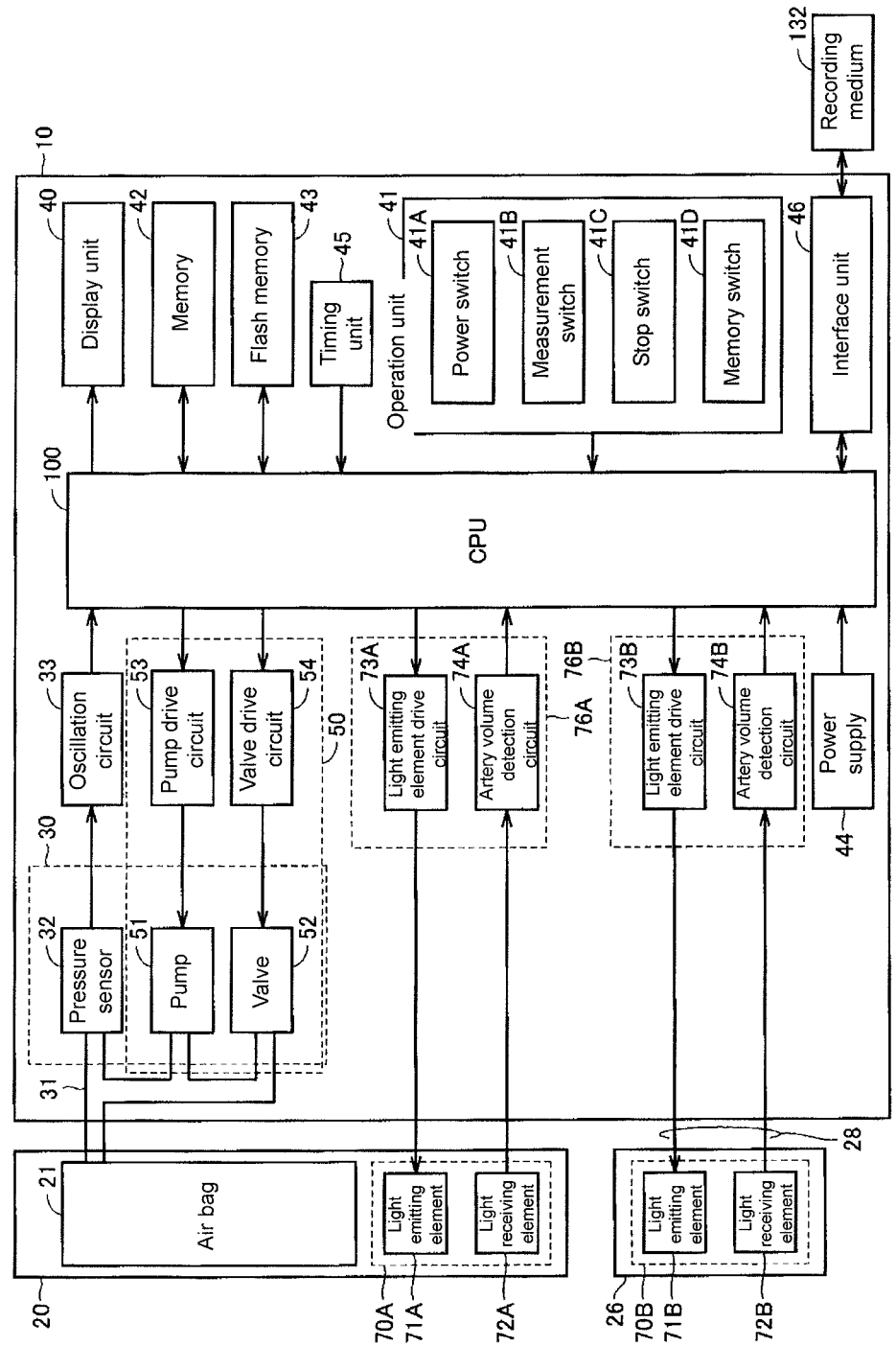
FIG. 3 is a block diagram showing the hardware configuration of the blood pressure information measurement device according to the first embodiment of the present invention.

FIG. 3 is a block diagram showing the hardware configuration of the blood pressure information measurement device 1 according to the first embodiment of the present invention.

With reference to FIG. 3, the cuff 20 of the blood pressure information measurement device 1 includes an air bag 21 and an artery volume sensor 70A for detecting the volume of the artery of the measurement site (wrist 302). The artery volume sensor 70A includes a light emitting element 71A and a light receiving element 72A. The light emitting element 71A irradiates the artery with light, and the light receiving element 72A receives the light (transmissive light) in which the light emitted by the light emitting element 71A transmits through the artery or the light (reflected light) reflected by the artery. The light emitting element 71A and the light receiving element 72A are arranged at a predetermined spacing on the inner side of the air bag 21.

The peripheral unit 26 includes an artery volume sensor 70B for detecting the volume of the artery of the peripheral site (finger base portion 304). The artery volume sensor 70B may have a configuration similar to the artery volume sensor 70A, and includes a light emitting element 71B and a light receiving element 72B. The functions of the light emitting element 71B and the light receiving element 72B are similar to the functions of the light emitting element 72A and the light receiving element 72B.

In the present embodiment, the artery volume sensor 70B is arranged in advance on the wrapping member for wrapping around the peripheral site, but the present invention is not limited thereto.

Both artery volume sensors 70A, 70B merely need to be able to detect the volume of the artery, and may detect the volume of the artery by an impedance sensor (impedance plethysmography). In this case, a plurality of electrodes (electrode pair for current application and electrode pair for voltage detection) for detecting the impedance of the site including the artery is arranged in place of the light emitting elements 71A, 71B and the light receiving elements 72A, 72B.

The air bag 21 is connected to an air system 30 through the air tube 31.

In addition to the display unit 40 and the operation unit 41, the main body 10 includes the air system 30, a CPU (Central Processing Unit) 100 for controlling each unit in a concentrated manner and for carrying out various calculation processes, a memory 42 for storing programs for causing the CPU 100 to perform a predetermined operation and various pieces of data, a non-volatile memory (e.g., flash memory) 43 for storing the measured blood pressure information, a power supply 44 for supplying power to the CPU 100, a timing unit 45 for performing the timing operation, and an interface unit 46 for reading and writing the program and data with respect to a removable recording medium 132.

The operation unit 41 includes a power switch 41A for receiving the input of instruction to turn ON or OFF the power, a measurement switch 41B for receiving the instruction to start the measurement, a stop switch 41C for receiving the instruction to stop the measurement, and a memory switch 41D for accepting the instruction to read out information such as blood pressure recorded in the flash memory 43.

The air system 30 includes a pressure sensor 32 for detecting the pressure (cuff pressure) in the air bag 21, a pump 51 for supplying air to the air bag 21 to pressurize the cuff pressure, and a valve 52 that opens and closes to exhaust or enclose the air of the air bag 21.

The main body 10 includes an artery volume detection unit 76A connected to the artery volume sensor 70A, an artery volume detection unit 76B connected to the artery volume sensor 70B, and also an oscillation circuit 33, a pump drive circuit 53, and a valve drive circuit 54 in relation to the air system 30.

The artery volume detection unit 76A is configured by a light emitting element drive circuit 73A and the artery volume detection circuit 74A. The artery volume detection unit 76B is configured by a light emitting element drive circuit 73B and the artery volume detection circuit 74B.

The light emitting element drive circuit 73A, 73B each causes the light emitting element 71A, 71B to emit light at a predetermined timing according to a command signal from the CPU 100. The artery volume detection circuit 74A, 74B detects the artery volume of the measurement site and the peripheral site by converting the output from the light receiving element 72A, 72B to a voltage value.

In the present embodiment, the artery volume signal of the measurement site obtained from the artery volume detection circuit 74A is expressed as "MPGdc". The artery volume change signal of the measurement site detected from the signal MPGdc is expressed as "MPGac". Similarly, the artery volume signal of the peripheral site obtained from the artery volume detection circuit 74B is expressed as "PPGdc". The artery volume change signal of the peripheral site detected from the signal PPGdc is expressed as "PPGac".

In the present embodiment, the description will be made assuming that the CPU 100 detects (calculates) the artery volume change signals MPGac and PPGac, but the artery volume change signals MPGac and PPGac may be detected in the artery volume detection circuit 74A and the artery volume detection circuit 74B.

The pressure sensor 32 is a capacitance type pressure sensor, where the capacitance value changes according to the cuff pressure. The oscillation circuit 33 outputs a signal of an oscillating frequency corresponding to the capacitance value of the pressure sensor 32 to the CPU 100. The CPU 100 converts the signal obtained from the oscillation circuit 33 to a pressure, and detects the pressure. The pump drive circuit 53 controls the drive of the pump 51 based on a control signal provided from the CPU 100. The valve drive circuit 54 performs the open/close control of the valve 52 based on a control signal provided from the CPU 100.

The pump 51, the valve 52, the pump drive circuit 53, and the valve drive circuit 54 configure an adjustment unit 50 for adjusting the pressure of the cuff 20 by pressurization and depressurization. The devices configuring the adjustment unit 50 are not limited to the above. For example, the adjustment unit 50 may include an air cylinder and an actuator for driving the air cylinder in addition to the above.

The air bag 21 is arranged in the cuff 20, but the fluid to be supplied to the cuff 20 is not limited to air and may be a liquid or gel. Alternatively, it is not limited to a fluid and may be uniform fine particles such as micro-beads.

(Regarding Function Configuration)

Figure 4:
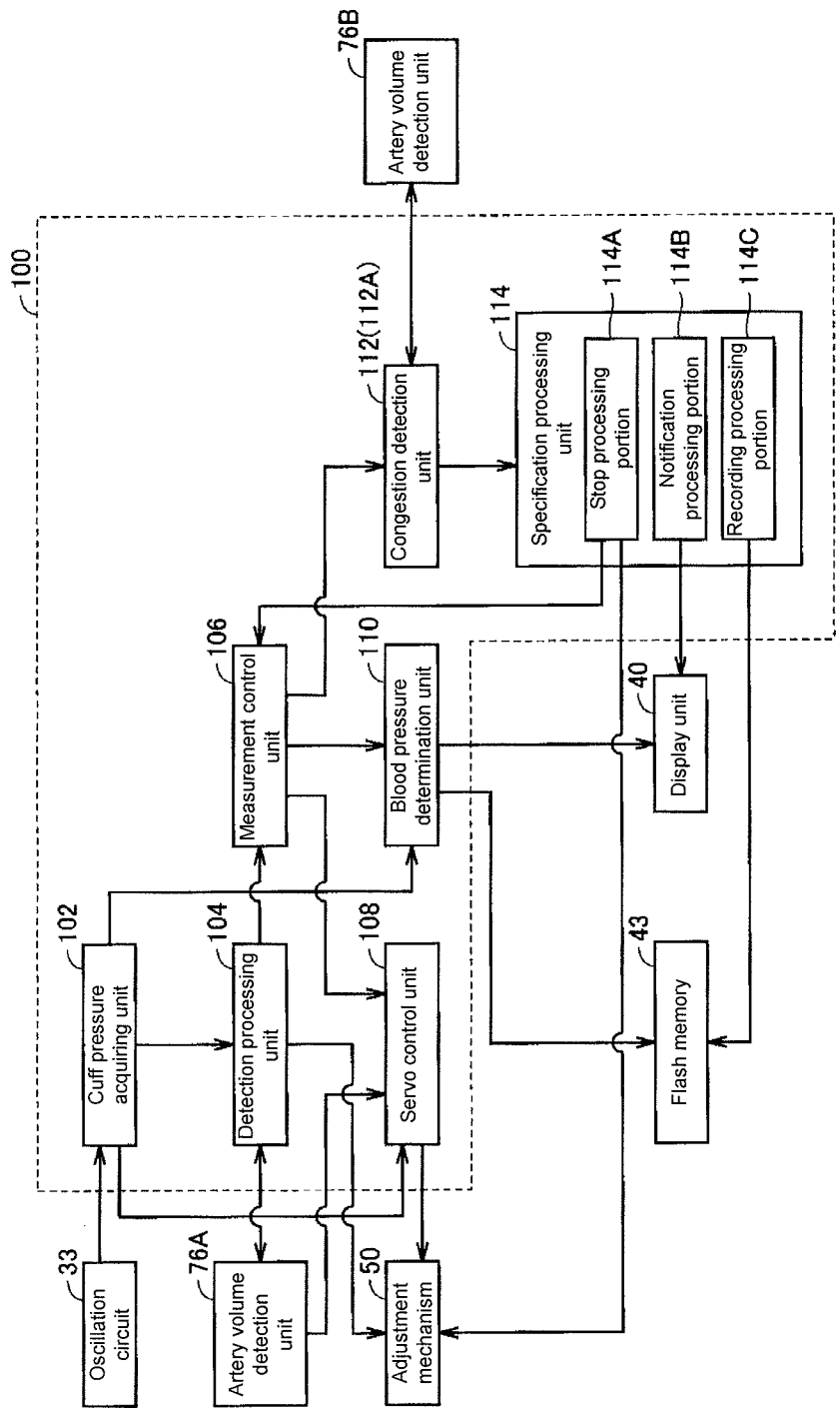
FIG. 4 is a function block diagram showing the function configuration of the blood pressure information measurement device according to the first embodiment of the present invention.

FIG. 4 is a function block diagram showing the function configuration of the blood pressure information measurement device 1 according to the first embodiment of the present invention.

With reference to FIG. 4, the CPU 100 includes a cuff pressure acquiring unit 102, a detection processing unit 104, a measurement control unit 106, a servo control unit 108, a blood pressure determination unit 110, a congestion detection unit 112, and a specification processing unit 114. In FIG. 4, only the peripheral hardware that directly exchanges signals and data with such function blocks is shown to simplify the description.

The cuff pressure acquiring unit 102 acquires the cuff pressure based on the signal from the oscillation circuit 33. More specifically, the cuff pressure is acquired by converting the signal of the oscillating frequency detected by the oscillation circuit 33 to a pressure. The acquired cuff pressure is outputted to the detection processing unit 104, the servo control unit 108, and the blood pressure determination unit 110.

The detection processing unit 104 performs the detection process of the control target value V0 and the initial cuff pressure PC0. The specific process by the detection processing unit 104 may be realized through a known method (e.g., Japanese Examined Patent Publication No. 1-31370, Japanese Unexamined Patent Publication No. 2008-36004).

The measurement control unit 106 performs the control for the blood pressure information measurement when the detection of the control target value (and initial cuff pressure) is finished. The measurement control unit 106 controls the operation of the servo control unit 108, the blood pressure determination unit 110, and the congestion detection unit 112.

The servo control unit 108 is connected to the adjustment unit 50 and the artery volume detection unit 76A, and performs the servo control under the control of the measurement control unit 106 so that the artery volume of the measurement site (value of the artery volume signal MPGdc) matches the control target value V0. That is, the pressure of the cuff 20 is feedback controlled so that the value of the artery volume change signal MPGac representing the AC component of the artery volume signal becomes "0".

The blood pressure determination unit 110 continuously determines (measures) the blood pressure for the period of the servo control under the control of the measurement control unit 106. Specifically, the artery volume signal MPGdc and the cuff pressure signal from the cuff pressure acquiring unit 102 are acquired in time-series. The cuff pressure at the time point when the amount of change (value of the artery volume change signal MPGac) of the artery volume of the measurement site becomes smaller than or equal to a predetermined value, that is, the cuff pressure when the artery wall is in the no-load state is determined as the blood pressure. This is the same as determining the cuff pressure at the time point when the difference between the value of the artery volume of the measurement site and the control target value V0 becomes smaller than or equal to a predetermined threshold value as the blood pressure.

The congestion detection unit 112 is connected to the artery volume detection unit 76B, and detects the congestion of the peripheral site in the period of the servo control (after at least the artery wall becomes the no-load state first) under the control of the measurement control unit 106. In the present embodiment, the congestion detection unit 112 detects the presence of the congestion using the artery volume change signal PPGac of the peripheral site.

The principle on the detection of the presence of congestion in the present embodiment will now be described.

When congestion occurs at the peripheral site, the blood does not reflux even when the inner pressure of the artery becomes close to the diastolic blood pressure. Thus, when congestion occurs at the peripheral site, a state in which the blood amount is greater than when the congestion is not occurring, that is, a state in which the artery volume is large occurs. Therefore, the amount of change in the artery volume, that is, the value of the artery volume change signal PPGac that occurs with change in the inner pressure of the artery from the diastolic blood pressure to the systolic blood pressure becomes smaller than when the congestion is not occurring. In the present embodiment, the "value of the artery volume change signal PPGac" is the value indicating the amplitude of the artery volume change signal PPGac. The "value of the artery volume change signal MPGac" is also the same.

The occurrence of congestion can be detected by detecting and monitoring the amount of change in the artery volume of the peripheral site with the artery volume sensor 70B of the peripheral site. Specifically, the values of the artery volume change signal PPGac at the beginning of measurement and at the current time are detected, and determination is made that the congestion has occurred if the ratio of the detected values is smaller than a predetermined value (e.g., 1/2).

Determination may be made that the congestion has occurred when the difference in the values of the artery volume change signal PPGac at the beginning of measurement and at the current time becomes greater than or equal to a predetermined value. Alternatively, the level of congestion may be classified by the level of the ratio or the difference of the values of the artery volume change signal PPGac.

The specification processing unit 114 executes a specific process based on the detection result by the congestion detection unit 112. In the present embodiment, the specification processing unit 114 executes only the function of a stop processing portion 114A. The stop processing portion 114A executes the process of stopping the measurement as a specific process when the congestion is detected by the congestion detection unit 112.

In FIG. 4, the function blocks of a notification processing portion 114B and a recording processing portion 114C (to be described in a second embodiment later) are also shown in the specification processing unit 114 for the sake of convenience, but are not included in the present embodiment.

The CPU 100 causes the light emitting elements 71A, 71B to emit light at a constant interval by transmitting a command signal to the light emitting element drive circuits 73A, 73B during a series of the measurement period (including detection period of control target value). In the present embodiment, however, the light emission of the light emitting element 71B may be carried out only during the period of the servo control.

The operation of each function block described above may be realized by executing the software stored in the memory 42, or at least one of the function blocks may be realized with hardware.

<Regarding Operation>

The operation of the blood pressure information measurement device 1 according to the first embodiment of the present invention will now be described in detail.

Figure 5:
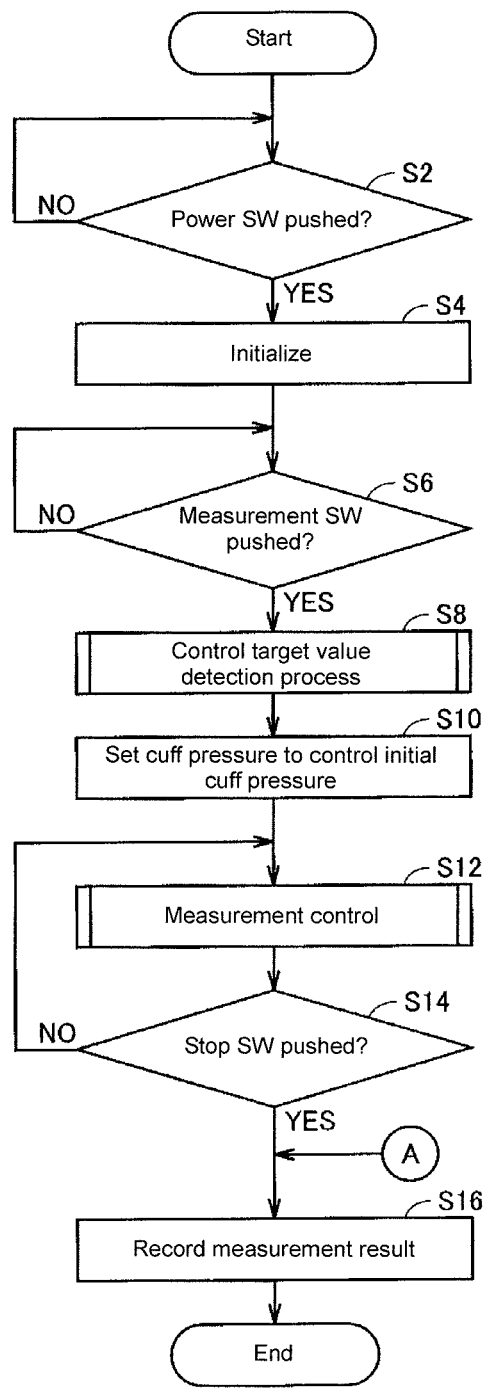
FIG. 5 is a flowchart showing a blood pressure measurement process according to the first embodiment of the present invention.

FIG. 5 is a flowchart showing the blood pressure measurement process according to the first embodiment of the present invention. The processes shown in the flowchart of FIG. 5 are stored in the memory 42 as a program in advance, and the function of the blood pressure measurement process is realized when the CPU 100 reads out and executes the program.

With reference to FIG. 5, the CPU 100 determines whether or not the power switch 41A is pushed (step S2). When it is determined that the power switch 41A is pushed (YES in step S2), the process proceeds to step S4.

In step S4, the CPU 100 performs the initialization process. Specifically, a predetermined region of the memory 42 is initialized, the air of the air bag 21 is exhausted, and 0 mmHg correction of the pressure sensor 32 is carried out.

After the initialization is finished, the CPU 100 determines whether or not the measurement switch 41B is pushed (step S6), and waits until the measurement switch 41B is pushed. The process proceeds to step S8 when it is determined that the measurement switch 41B is pushed (YES in step S6).

In step S8, the detection processing unit 104 executes the control target value detection process. In other words, the control target value V0 and the initial cuff pressure PC0 are detected. The control target value detection process will be described with reference to FIG. 6 and FIGS. 7(A) to 7(C).

Figure 6:
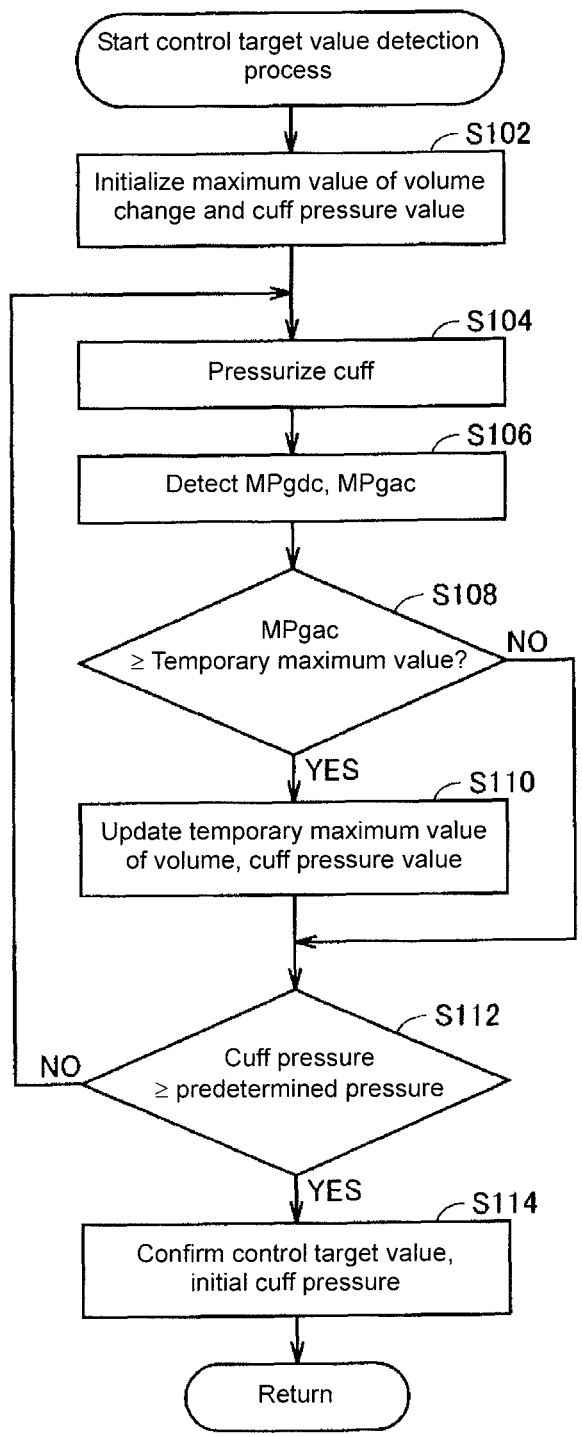
FIG. 6 is a flowchart showing a control target value detection process in the first embodiment of the present invention.
Figure 7:
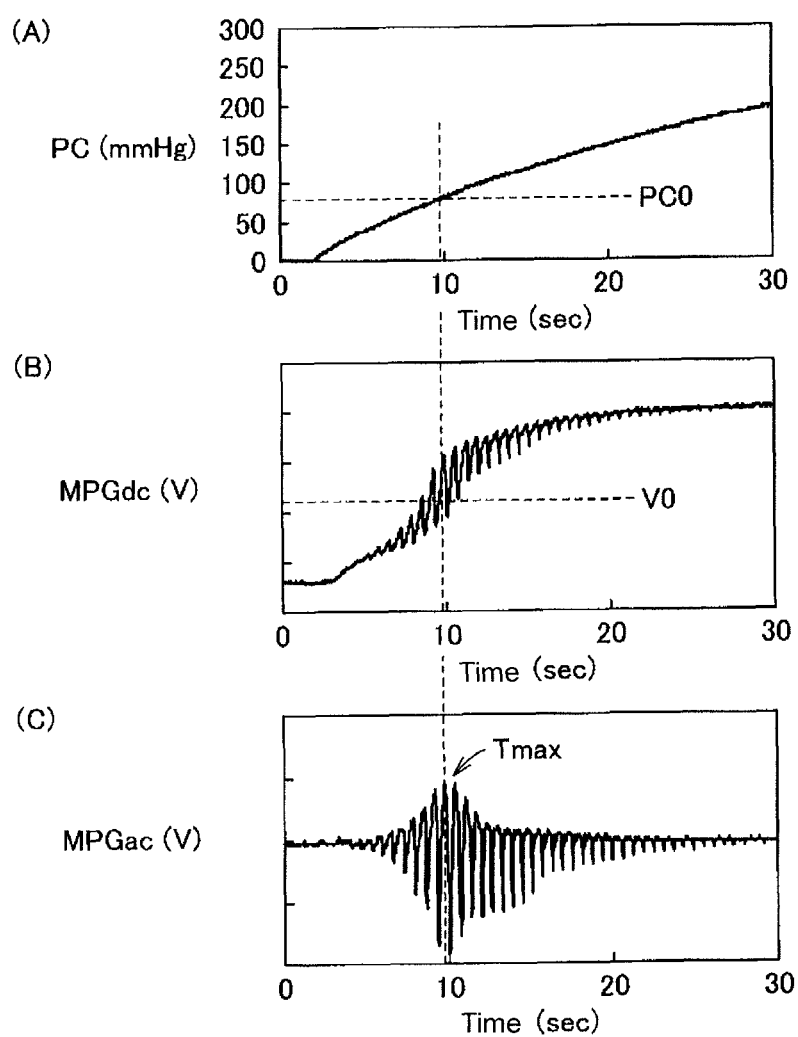
FIGS. 7(A) to 7(C) are views describing the control target value detection process of the first embodiment of the present invention.

FIG. 6 is a flowchart showing the control target value detection process in the first embodiment of the present invention. FIGS. 7(A) to 7(C) are views describing the control target value detection process of the first embodiment of the present invention. FIG. 7(A) shows the cuff pressure PC along the time axis. FIG. 7(B) shows the artery volume signal MPGdc of the measurement site along the same time axis as FIG. 7(A). FIG. 7(C) shows the artery volume change signal MPGac of the measurement site along the same time axis as FIG. 7(A).

With reference to FIG. 6, the detection processing unit 104 initializes the maximum value of the amplitude of the artery volume change signal MPGac and the cuff pressure value stored in a predetermined region of the memory 42 (step S102). The maximum value of the amplitude of the artery volume change signal MPGac is updated as needed in the following process, and the value until ultimately confirmed as the maximum value is referred to as "temporary maximum value of volume".

The pump drive circuit 53 is then driven to pressurize the cuff pressure (step S104).

The detection processing unit 104 detects the signal (artery volume signal MPGdc from the artery volume detection circuit 74A at the stage of pressurizing the cuff pressure (step S106). The detection processing unit 104 detects the artery volume change signal MPGac obtained from the artery volume signal MPGdc.

The detection processing unit 104 determines whether or not the value (amplitude value) of the artery volume change signal MPGac is greater than or equal to the temporary maximum value of volume stored in the memory 42 (step S108). When it is determined that the artery volume change signal MPGac is greater than or equal to the temporary maximum value of volume (YES in step S108), the process proceeds to step S110. When it is determined that the artery volume change signal MPGac is smaller than the temporary maximum value of volume (NO in step S108), the process proceeds to step S112.

In step S110, the detection processing unit 104 updates the temporary maximum value of volume, and overwrites and records the cuff pressure at the relevant time point. After this process is finished, the process proceeds to step S112.

In step S112, the detection processing unit 104 determines whether or not the cuff pressure is greater than or equal to a predetermined value (e.g., 200 mmHg). When it is determined that the cuff pressure has not reached the predetermined value (NO in step S112), the process returns to step S104. When it is determined that the cuff pressure is greater than or equal to a predetermined value (YES in step S112), the process proceeds to step S114.

In step S114, the detection processing unit 104 confirms the temporary maximum value of volume ultimately recorded in step S110 as the maximum value, and confirms the cuff pressure value at the time point (time point indicated as "Tmax" in FIG. 7) when the maximum value is detected as the initial cuff pressure PC0. The detection processing unit 104 also confirms the average value of the artery volume signal MPGdc at the time point Tmax as the control target value V0.

After the process of step S114 is finished, the process returns to the main routine.

Referring again to FIG. 5, after the control target value V0 and the initial cuff pressure PC0 are determined, the CPU 100 sets the cuff pressure to the initial cuff pressure PC0 (step S10).

Thereafter, a substantial measurement control is executed (step S12). In the present embodiment, the measurement control is executed until the stop switch 41C is pushed (NO in step S14).

The measurement control in the present embodiment will be described in detail with reference to FIG. 8 and FIG. 9.

Figure 8:
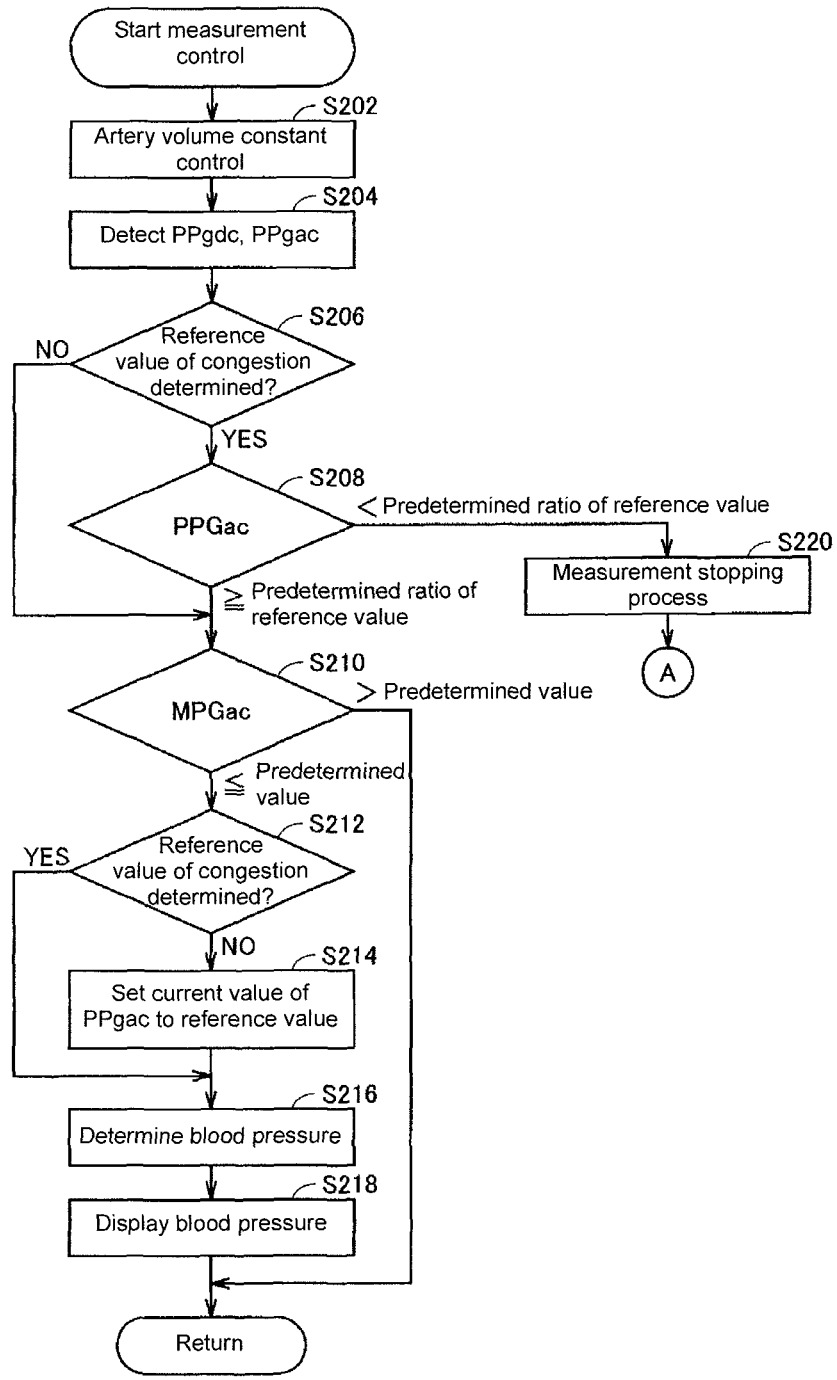
FIG. 8 is a flowchart showing the measurement control in the first embodiment of the present invention.
Figure 9:
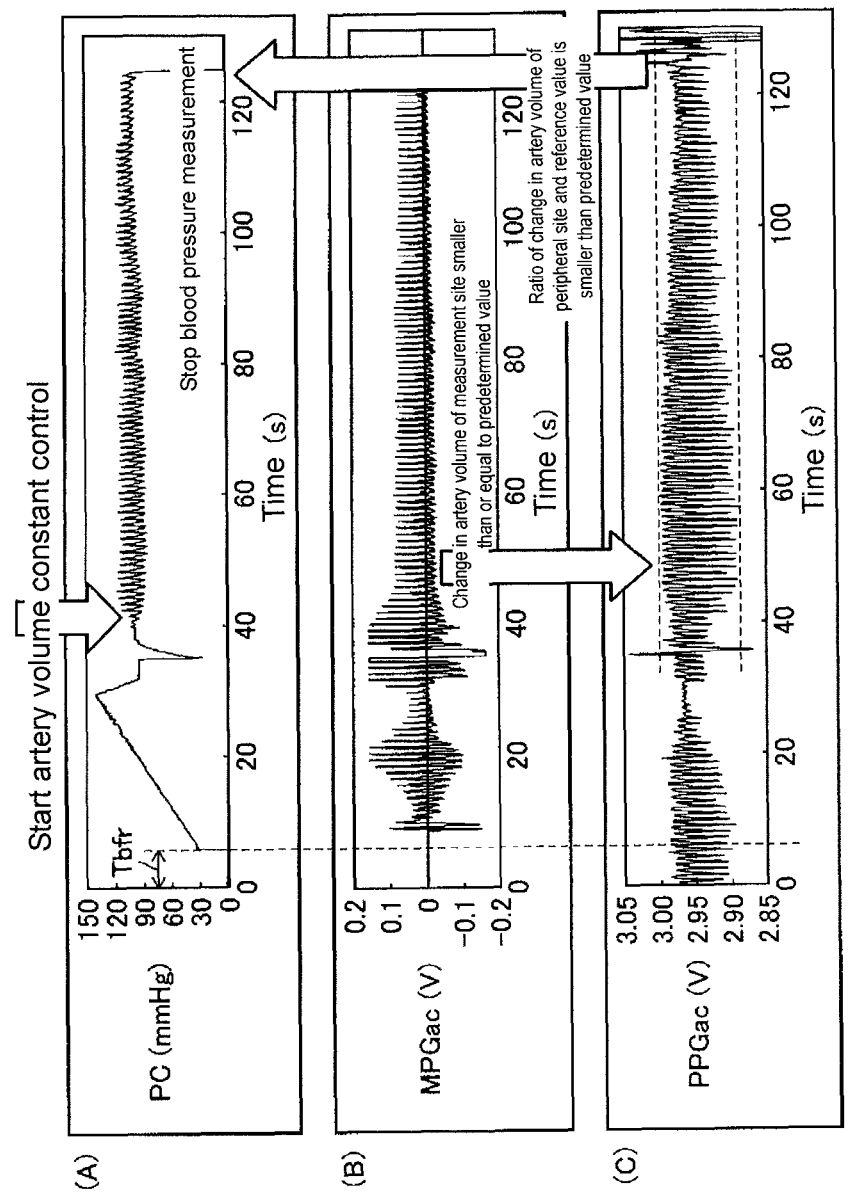
FIGS. 9(A) to 9(C) are views describing the measurement control of the first embodiment of the present invention.

FIG. 8 is a flowchart showing the measurement control in the first embodiment of the present invention. FIGS. 9(A) to 9(C) are views describing the measurement control of the first embodiment of the present invention. FIG. 9(A) shows the cuff pressure PC along the time axis. FIG. 9(B) shows the artery volume change signal MPGac of the measurement site along the same time axis as FIG. 9(A). FIG. 9(C) shows the artery volume change signal PPGac of the peripheral site along the same time axis as FIG. 9(A).

With reference to FIG. 8, the servo control unit 108 executes an artery volume constant control (step S202) so that the artery volume signal MPGdc of the measurement site matches the control target value V0. That is, the cuff pressure is feedback controlled so that the value of the artery volume change signal MPGac of the measurement site shown in FIG. 9(B) becomes smaller than or equal to a predetermined value (to become substantially zero) by controlling the adjustment unit 50. The artery volume change signal MPGac can be obtained by filtering the artery volume signal MPGdc.

The congestion detection unit 112 then detects the artery volume signal PPGdc of the peripheral site, and detects (calculates) the artery volume change signal PPGac for every heart beat as shown in FIG. 9(C) from the detected artery volume signal PPGdc (step S204). The artery volume change signal PPGac also can be obtained by filtering the artery volume signal PPGdc.

The congestion detection unit 112 then determines whether or not the reference value of the congestion is determined (step S206). The process proceeds to step S208 when the reference value has been determined (YES in step S206), and the process proceeds to step S210 when the reference value has not yet been determined (NO in step S206).

In step S208, the congestion detection unit 112 determines whether or not the value of the artery volume change signal PPGac (amount of change in the artery volume of the peripheral site) is greater than or equal to a predetermined ratio (e.g., 1/2) of the reference value. The method of determining the reference value will be described later. The process proceeds to step S210 if the value of the artery volume change signal PPGac satisfies the relevant condition (in step S208, "predetermined ratio of reference value").

In step S210, the blood pressure determination unit 110 determines whether or not the value (amount of change in artery volume of the measurement site) of the artery volume change signal MPGac of the measurement site is smaller than or equal to the predetermined value. If the value of the artery volume change signal MPGac satisfies the condition ("≤ predetermined value" in step S210), the process proceeds to step S212. If the value of the artery volume change signal MPGac does not satisfy the condition ("> predetermined value" in step S210), determination is made that the artery wall is not in the no-load state, and the process returns to step S14 of the main routine of FIG. 5.

In step S212, the congestion detection unit 112 determines whether or not the reference value of the congestion is determined. When the reference value has been determined (YES in step S212), the process proceeds to step S216. When the reference value has not yet been determined (NO in step S212), the value (amplitude value) of the current artery volume change signal PPGac of the peripheral site is set as the reference value (step S214). That is, when the value of the artery volume change signal MPGac of the measurement site becomes smaller than or equal to the predetermined value for the first time since the artery volume constant control started (i.e., when detected that the artery wall is in the no-load state), the value of the artery volume change signal PPGac at the relevant time point is set as the reference value for the determination of the congestion. The reference value may be set with the amount of change in the artery volume for one beat, or may be set with a statistical value (e.g., average value) of the amount of change in the artery volume for a plurality of beats (e.g., three beats).

After the above process is finished, the process proceeds to step S216.

In step S216, the blood pressure determination unit 110 determines the current cuff pressure as the blood pressure. The successive blood pressure values are thereby obtained, and the blood pressure waveform is obtained as a result. The cuff pressure determined as the blood pressure is recorded in time series in a predetermined region of the memory 42.

The blood pressure determination unit 110 then displays the local minimum value and the local maximum value of the cuff pressure for every heart beat as the diastolic blood pressure and the systolic blood pressure, respectively, on the predetermined region of the display unit 40 (step S218). The information displayed on the display unit 40 is not limited to the blood pressure value, and may be a blood pressure waveform along the time axis.

After the process of step S218 is finished, the process returns to step S14 of the main routine of FIG. 5.

If the value of the artery volume change signal PPGac does not satisfy the above condition in step S208 described above ("< predetermined ratio of reference value" in step S208), the stop processing portion 114A executes the measurement stopping process (Step S220). Specifically, for example, the stop processing portion 114A notifies the measurement control unit 106 to stop the measurement, and also transmits the control signal to the valve drive circuit 54 (adjustment unit 50) to rapidly exhaust the air in the air bag 21. The measurement control unit 106 terminates the control for the blood pressure information measurement when receiving the notification. After the measurement is stopped, the process proceeds to step S16 of the main routine of FIG. 5.

Referring again to FIG. 5, when the stop switch 41C is pushed in step S14 (YES in step S14), the process proceeds to step S16.

In step S16, the CPU 100 records the blood pressure value (cuff pressure value) recorded in time series in the memory 42 before the measurement is stopped in the flash memory 43 as the measurement result.

The blood pressure measurement process in the present embodiment is then terminated.

In the present embodiment, the successively obtained blood pressure values are recorded in the flash memory 43 as the blood pressure information, as described above, but other blood pressure information may be recorded in the flash memory 43. The other blood pressure information may be the systolic blood pressure and the diastolic blood pressure for every beat. The blood pressure information may be an AI (Augmentation Index) that can be calculated by applying a predetermined algorithm on the blood pressure waveform based on the successively obtained blood pressure values.

Furthermore, unless the measurement is stopped (canceled) by the stop processing portion 114A, the measurement control is continued until the stop switch 41C is pushed in the present embodiment, but the measurement control may be continued until elapse of a predetermined time from the start of the artery volume constant control.

<Regarding Data Structure>

The data structure of each measurement data stored in the flash memory 43 by the blood pressure measurement process above will now be described.

Figure 10:
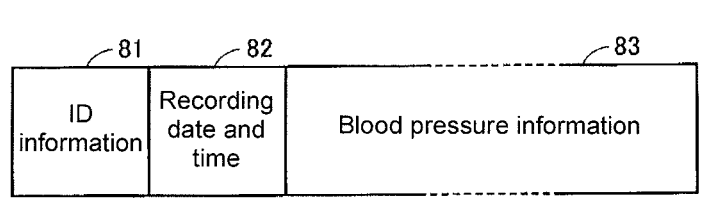
FIG. 10(A) is a view showing a data structure of each measurement data in the blood pressure information measurement device of the first embodiment of the present invention.
FIG. 10(B) is a view showing a data structure of the blood pressure information field contained in the measurement data.

FIG. 10(A) is a view showing the data structure of each measurement data in the blood pressure information measurement device 1 of the first embodiment of the present invention.

With reference to FIG. 10(A), each measurement data 80 stored in the flash memory 43 includes three fields 81 to 83 of "ID information", "recording date and time", and "blood pressure information" by way of example. Briefly describing the content of each field, the "ID information" field 81 stores identification number and the like for specifying each measurement data, and the "recording date and time" field 82 stores information such as measurement start date and time, measurement period, and the like of each measurement data timed by the timing unit 45. The "blood pressure information" field 83 stores the time series blood pressure data, that is, the blood pressure waveform data.

FIG. 10(B) is a view showing the data structure of the blood pressure information field 83 contained in the measurement data.

With reference to FIG. 10(B), the blood pressure information field includes a region 831 for storing the "time data" and a region 832 for storing the "blood pressure data".

A plurality of pieces of time data 1, 2, 3, ... N corresponding to the sampling period are stored in the region 831. The blood pressure data BD(1), BD(2), ... BD(n) are stored in the region 832 in correspondence with the time data of the region 831. In the region 832, the region indicated with "-" shows that the value of the artery volume change signal MPGac at the relevant time point exceeds a predetermined value and is not recorded as a blood pressure.

The storage mode is not limited to such an example, and the time (clock time) and the blood pressure merely need to be stored in correspondence to each other.

The blood pressure information is stored in the flash memory 43 in such a manner. The blood pressure information also includes an index that can be calculated from the blood pressure waveform such as pulse and AI in addition to the blood pressure value of the systolic blood pressure, the diastolic blood pressure, the average blood pressure, and the like.

As described above, the presence of congestion can be determined by detecting and monitoring the amount of change of the artery volume of the peripheral site during the measurement control, that is, during the period of feedback control according to the present embodiment. When it is determined that congestion occurred, the measurement process is automatically stopped (canceled). Thus, only the reliable blood pressure value can be recorded as the measurement result. Furthermore, the tissues on the peripheral side can be prevented from degenerating and necrotizing as a result of the congestive state continued for a long time.

Moreover, according to the present embodiment, the presence of congestion can be appropriately detected for each person to be measured because the waveform for the artery volume of the peripheral site is monitored for every measurement.

<Variant>

In the first embodiment, the congestion is detected based on the amount of change in the artery volume of the peripheral site, that is, the value of the artery volume change signal PPGac, but the congestion is detected based on the artery volume of the peripheral site itself, that is, the value of the artery volume signal PPGdc in the variant of the present embodiment.

Only the portion different from the first embodiment will be described below with reference to FIG. 11 and FIG. 12. In the present variant, the congestion detection unit 112 is described as a congestion detection unit 112A because the function of the congestion detection unit 112 of the first embodiment is different.

The principle on the detection of the presence of congestion in the variant of the present embodiment will now be described.

When congestion occurs at the peripheral site, the blood does not reflux even when the inner pressure of the artery becomes close to the diastolic blood pressure. Thus, when congestion occurs at the peripheral site, a state in which the blood amount is greater than when the congestion is not occurring, that is, a state in which the artery volume is large, occurs. Therefore, the artery volume of the peripheral site is assumed to be correlated with the extent of congestion.

Therefore, the occurrence of congestion can be detected by detecting and monitoring the artery volume of the peripheral site with the artery volume sensor 70B of the peripheral site.

Specifically, the artery volumes at the beginning of measurement and at the current time are detected, and determination is made that the congestion has occurred if the ratio of the detected values is smaller than a predetermine value (e.g., 0.8).

Determination may be made that the congestion has occurred when the difference in the artery volumes at the beginning of measurement and at the current time becomes greater than or equal to a predetermined value. Alternatively, the level of congestion may be classified by the level of the ratio or the difference of the artery volumes.

Figure 11:
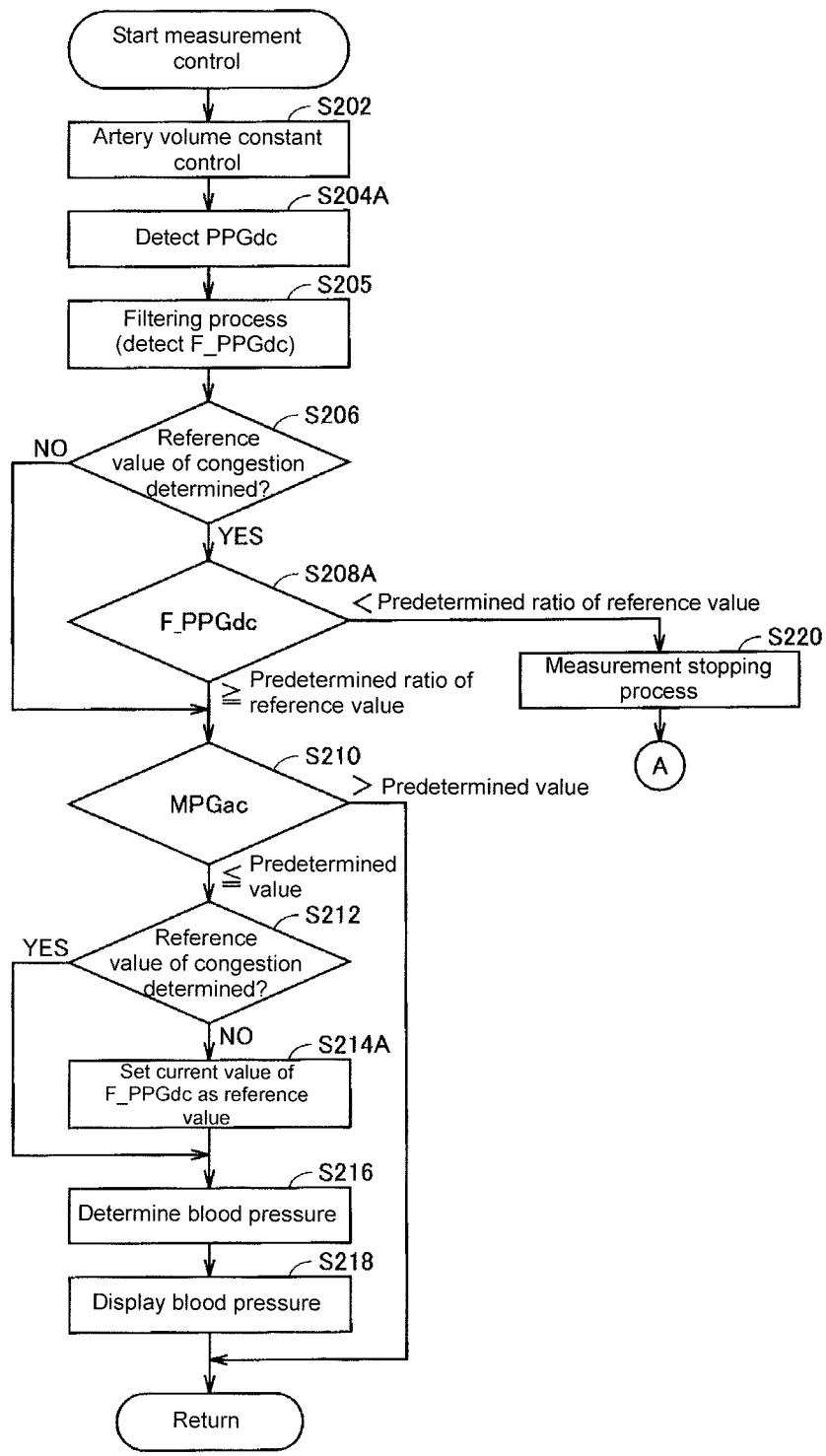
FIG. 11 is a flowchart showing the measurement control in a variant of the first embodiment of the present invention.
Figure 12:
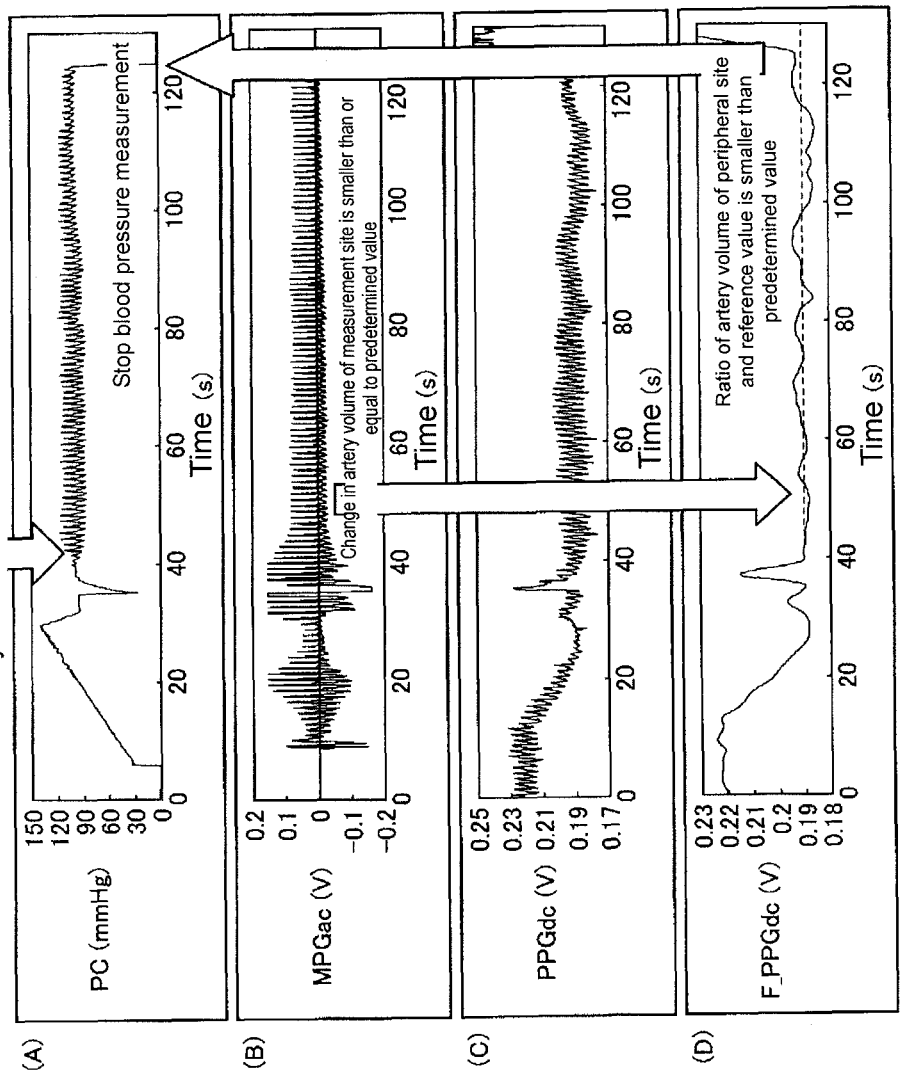
FIGS. 12(A) to 12(D) are views for describing the measurement control in the variant of the first embodiment of the present invention.

FIG. 11 is a flowchart showing the measurement control in the variant of the first embodiment of the present invention. In FIG. 11, the same step numbers are denoted for the processes similar to the processes shown in FIG. 8. The description thereof thus will not be repeated.

FIGS. 12(A) to 12(D) are views for describing the measurement control in the variant of the first embodiment of the present invention. FIG. 12(A) shows the cuff pressure PC along the time axis. FIG. 12(B) shows the artery volume change signal MPGac of the measurement site along the same time axis as FIG. 12(A). FIG. 12(C) shows the artery volume signal PPGdc of the peripheral site along the same time axis as FIG. 12(A). FIG. 12(D) shows the artery volume signal F_PPGdc of the flattened (filtered) peripheral site along the same time axis as FIG. 12(A).

With reference to FIG. 11, steps S204A, 208A, S214A are executed in place of steps S204, S208, S214, respectively, compared to FIG. 8. Step S205 is inserted between step S204A and step S206.

In step S204A, only the artery volume signal PPGdc of the peripheral site is detected. The change in volume involved in change in blood pressure is superimposed on the detected artery volume signal PPGdc, as shown in FIG. 12(C). To facilitate the subsequent comparing process, the congestion detection unit 112A calculates the signal in which the amount of change in volume involved in the change in blood pressure is removed from the detected artery volume signal PPGdc in step S205. Specifically, the amount of change in volume is removed by performing the low pass filtering process on the artery volume signal PPGdc. The resultant signal is shown as the artery volume signal "F_PPGdc" in FIG. 12(D).

In step 5208A, whether or not the value of the artery volume signal F_PPGdc is greater than or equal to a predetermined ratio (e.g., 0.8) is determined. The method of determining the reference value will be described later.

If the value of the artery volume signal F_PPGdc satisfies the above condition ("≥ predetermined ratio of reference value" in step S208A), the process proceeds to step S210 to continue the measurement process. If the above condition is not satisfied ("< predetermined ratio of reference value" in step S208A), the process proceeds to step S220 to stop the measurement process.

In the present embodiment, the measurement is stopped when the value of the artery volume signal F_PPGdc is smaller than the predetermined ratio of the reference value because there is adopted a sensor in which the value of the artery volume signals PPGdc, F_PPGdc becomes smaller as the volume of the artery at the peripheral site becomes greater. However, the measurement may be stopped when the value of the artery volume signal F_PPGdc is greater than or equal to the predetermined ratio (e.g., 120%) of the reference value if there is adopted a sensor in which the value of the artery volume signals PPGdc, F_PPGdc becomes greater as the volume of the artery at the peripheral site becomes greater.

In step S214A, the congestion detection unit 112A sets the current value of the artery volume signal F_PPGdc of the peripheral site as the reference value. That is, in this case as well, when the value of the artery volume change signal MPGac of the measurement site becomes smaller than or equal to a predetermined value (i.e., when detection is made that the artery wall is in the no-load state) for the first time since the artery volume constant control is started, the value of the artery volume signal F_PPGdc at the relevant time point is set as the reference value for determining the congestion. The reference value may be set with the value of a single artery volume signal F_PPGdc or a statistical value (e.g., average value) of the values of a plurality (e.g., three) of artery volume signals PPGdc.

In the present variant, the measurement process is stopped if the artery volume signal F_PPGdc becomes smaller than the predetermined ratio of the reference value even once in step S208A, but the process transitions to the stopping process only when the artery volume signal F_PPGdc becomes smaller than the predetermined ratio of the reference value consecutively for a plurality of times (e.g., three times). This is because the artery volume sometimes changes by breathing. In FIG. 12(D), the blood pressure measurement is stopped when the above state is detected consecutively for three times. A similar process may be carried out in the first embodiment described above.

In the present variant, the temporal change in the artery volume of the peripheral site is determined by flattening the artery volume signal PPGdc of the peripheral site, but the present invention is not limited to this method. For example, the temporal change in the artery volume may be determined from an envelope curve connecting the local maximum points of the artery volume signal PPGdc.

[Second Embodiment]

In the first embodiment and the variant thereof, the measurement stopping process is carried out when congestion is detected, but the process of outputting the congestion information is carried out based on the detection result of the congestion in the second embodiment.

The configuration and the basic operation of the blood pressure information measurement device according to the present embodiment are similar to the first embodiment. Therefore, only the portion different from the first embodiment will be described below.

In the present embodiment, the CPU 100 has a function of the notification processing portion 114B and/or the recording processing portion 114C in place of the stop processing portion 114A shown in FIG. 4. In the following description, a case where the specification processing unit 114 of the CPU 100 has the functions of both the notification processing portion 114B and the recording processing portion 114C will be described.

Figure 13:
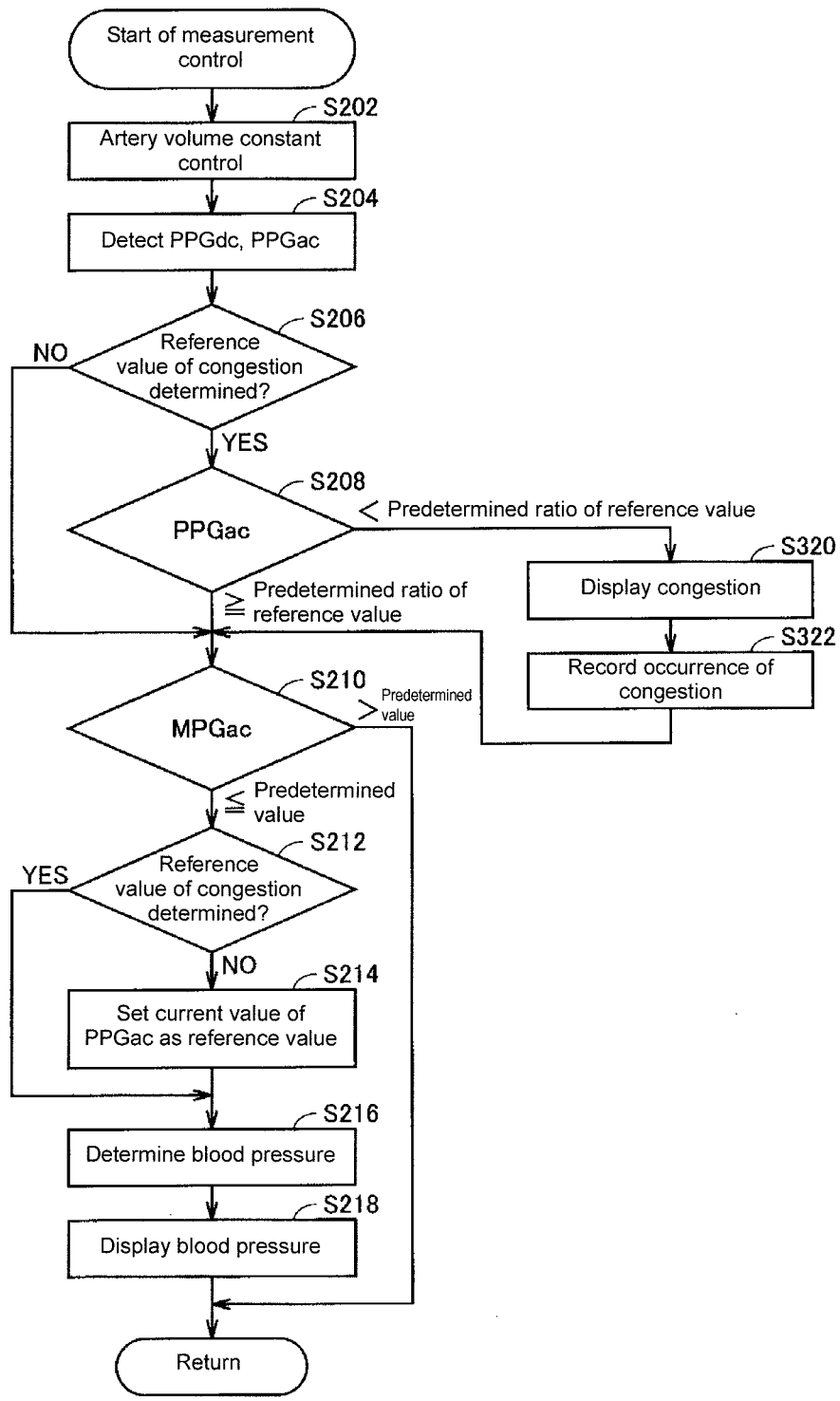
FIG. 13 is a flowchart showing a measurement control according to a second embodiment of the present invention.

FIG. 13 is a flowchart showing the measurement control in the second embodiment of the present invention. In FIG. 13, the same step numbers are denoted for the processes similar to the processes shown in FIG. 8. Therefore, the description thereof will not be repeated.

With reference to FIG. 13, in the present embodiment, the processes of steps S320 and S322 are executed in place of step S220 of the first embodiment.

Figure 14:
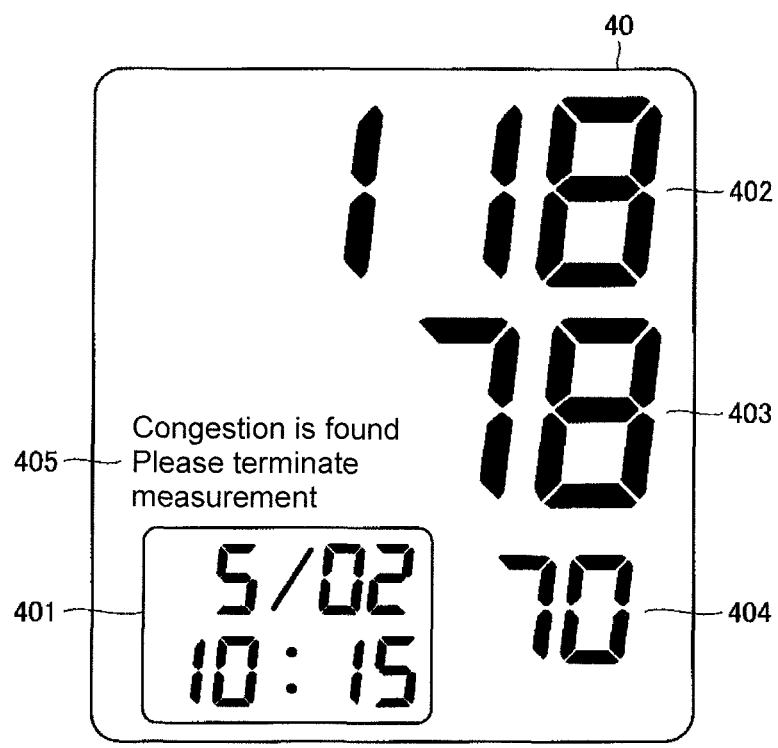
FIG. 14 is a view showing a display example of congestion.

In step S320, the notification processing portion 114B displays that the congestion has occurred in a predetermined region of the display unit 40. FIG. 14 is a view showing a display example of the congestion.

With reference to FIG. 14, the current date and time is displayed in a region 401 of the display unit 40. The current systolic blood pressure and diastolic blood pressure based on the determination result in step S216 are displayed in regions 402, 403 of the display unit 40, respectively. The pulse rate calculated through a known method is displayed in a region 404 of the display unit 40.

Furthermore, in the present embodiment, a message "Congestion is found. Please terminate measurement" is displayed in a region 405 of the display unit 40. A message is displayed in this case, but a predetermined mark may be displayed as long as the occurrence of congestion can be recognized. Alternatively, the congestion is notified by display, but the congestion may be notified by audio or light with an audio output unit or an LED (not shown).

After the process of step S320 is finished, the identification information indicating that the congestion has occurred is recorded in the memory 42 in correspondence with the time data in step S322. Through such processes, the identification information (e.g., congestion flag) for identifying the presence of detection of the congestion can be recorded in the flash memory 43 in correspondence with the blood pressure in step S16 of the main routine (FIG. 5).

The processing order of steps S320 and S322 may be reversed or may be executed in parallel.

Figure 15:
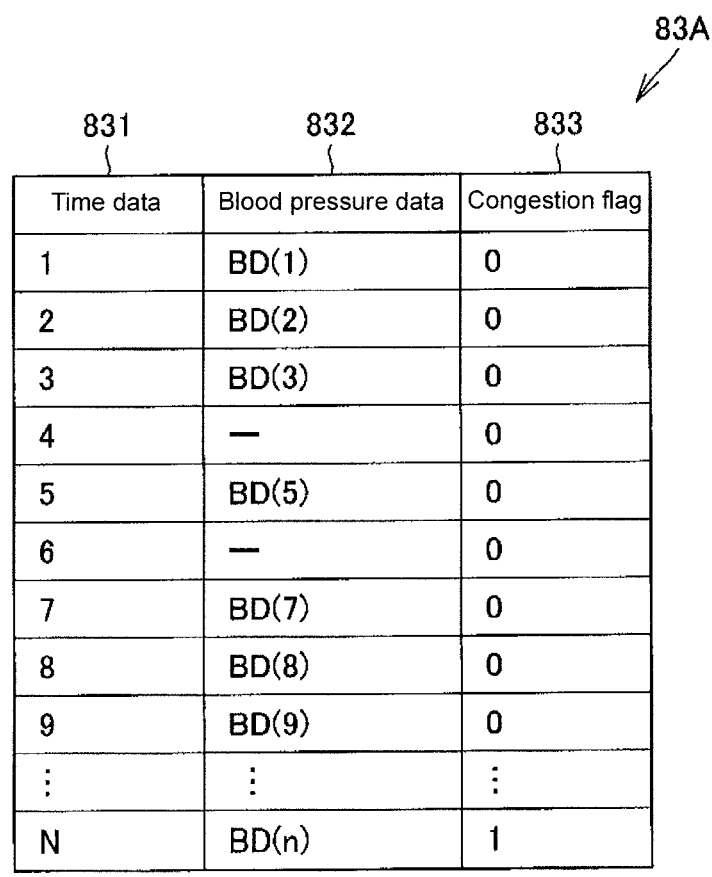
FIG. 15 is a view showing a data structure of a blood pressure information field contained in the measurement data according to a second embodiment of the present invention.

A data structure example of the blood pressure information field 83A contained in the measurement data in the second embodiment is shown in FIG. 15.

With reference to FIG. 15, the blood pressure information field 83A includes a region 833 for storing the "congestion flag" in addition to the region 831 for storing the "time data" and the region 832 for storing the "blood pressure data".

In the region 833, "0" indicating that the congestion is not detected or "1" indicating that the congestion is detected is stored in correspondence with each pair of the time data in the region 831 and the blood pressure data in the region 822. Each blood pressure data and the data indicating the presence of the congestion are thereby stored in correspondence with each other.

When the systolic blood pressure and the diastolic blood pressure for every beat are stored in the flash memory 43, the identification information indicating the presence of the congestion may be stored for every beat.

As described above, in the present embodiment, the stopping of the measurement is urged on the user rather than automatically stopping the measurement even when the congestion is detected. Therefore, the user will not be bewildered when the measurement is suddenly interrupted. However, if the instruction to stop the measurement from the user is late, the measurement will be continued with the congestion occurring. As a result, the blood pressure of low reliability will be recorded. In the present embodiment, however, the portion where the congestion is not occurring and the portion where the congestion is occurring can be displayed in an identifiable manner when subsequently displaying the measurement result, and the like, because the information on the presence of the occurrence of congestion is also recorded in correspondence with the blood pressure value. A doctor looking at the measurement result thus can easily recognize whether the data being displayed has high reliability or not.

The notifying process and the recording process are both performed in the present embodiment, but only one of the notifying process and the recording process may be performed. When performing only the notifying process, the blood pressure determination process may not be executed when the congestion is detected. The following process may be carried out in combination with the process of the first embodiment. In other words, when the congestion is detected, such a detection may be notified and the measurement may be stopped after elapse of a predetermined time.

Alternatively, the congestion detection unit 112 may further determine the congestion level, and the information indicating the congestion level may be displayed and recorded. The display example of such a case is shown in FIGS. 16(A) and 16(B).

Figure 16:
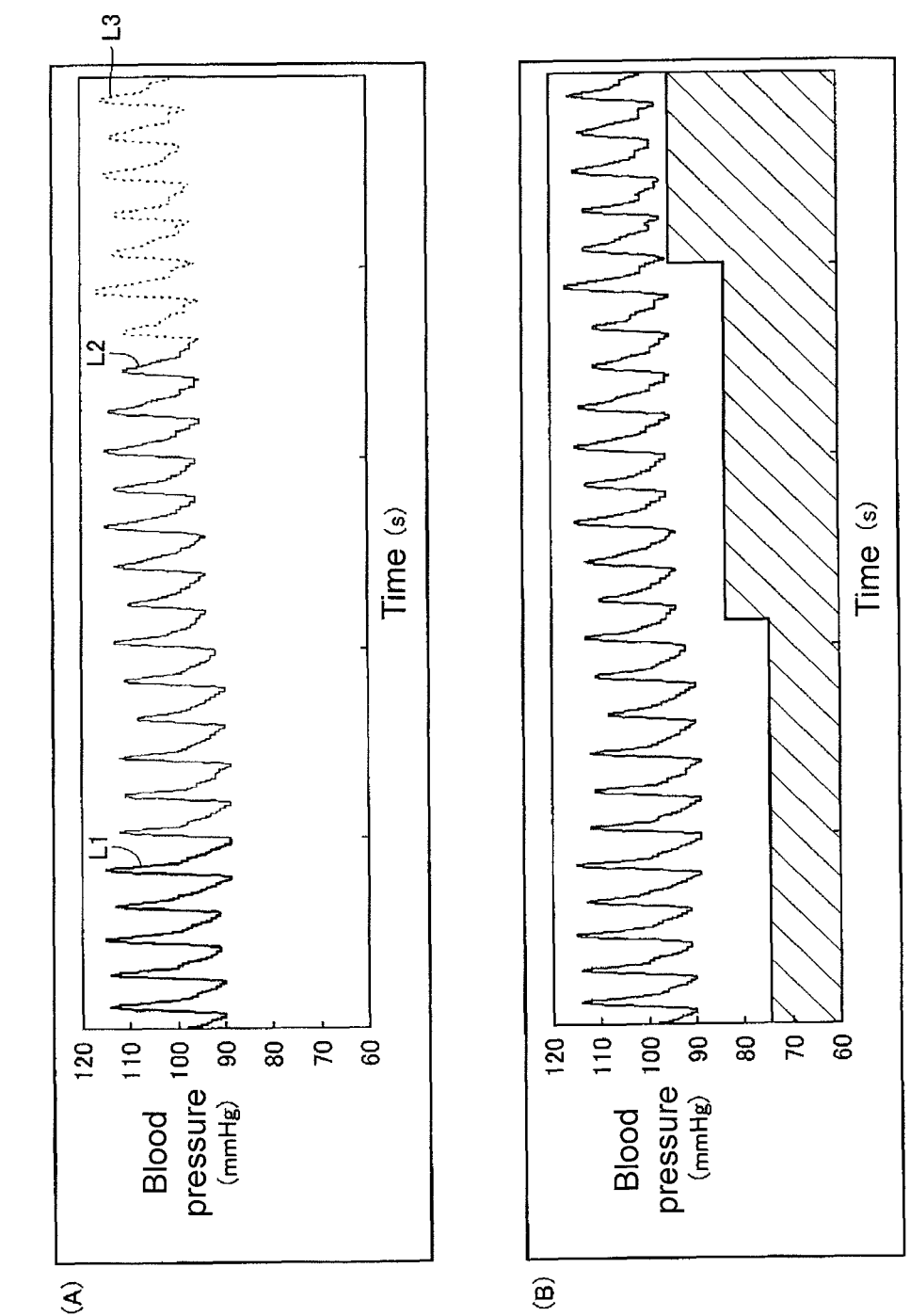
FIGS. 16(A) and 16(B) are views showing a display example of the congestion level.

With reference to FIG. 16(A), the line type to be drawn on the display unit 40 may be differed according to the congestion level. With reference to FIG. 16(B), the congestion level maybe displayed in a bar graph in correspondence with the portion where the congestion level of the blood pressure waveform being displayed differs.

The determination of the congestion level may be such that the level is 1 if the current value of the artery volume change signal PPGac is ¼ to ⅓, the level is 2 if the current value is ⅓ to ½, and the level is 3 if the current value is smaller than ½ of the value at the beginning of the measurement.

In such a case, if the congestion level is greater than or equal to 1, this may be displayed and the measurement may be stopped at the time point when the congestion level becomes 3.

The variant of the first embodiment and the second embodiment may be combined.

In the first embodiment, the variant thereof, and the second embodiment, the time point at which the no-load state is detected for the first time from the start of the servo control is the time point of setting the reference value for the determination of congestion (i.e., at the time of beginning of measurement). However, the beginning of measurement is not limited to such a time point (case), and may be a time point (time point Tmax of FIG. 7) at which the target value of the servo control is detected. In this case, the CPU 100 (congestion detection unit 112, 112A) executes the detection of the light emission of the light emitting element 71B and the signal from the light receiving element 72B even during the period in which the process by the detection processing unit 104 is being performed.

Alternatively, the beginning of measurement may be before the start of process by the detection processing unit 104. That is, with reference to FIG. 9(A), the beginning of measurement may be the time point (period Tbfr in which cuff pressure is 0 mmHg) before raising the cuff pressure to detect the control target value. In this case, the CPU 100 (congestion detection unit 112, 112A) may execute the detection of the light emission of the light emitting element 71B and the signal from the light receiving element 72B even during the period from when the measurement switch 41B is pushed until the process by the detection processing unit 104 is performed.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

DESCRIPTION OF REFERENCE NUMERALS

1 blood pressure information measurement device
10 main body
20 cuff
21 air bag
26 peripheral unit
28 cord
30 air system
31 air tube
32 pressure sensor
33 oscillation circuit
40 display unit
41 operation unit
41A power switch
41B measurement switch
41C stop switch
41D memory switch
42 memory
43 flash memory
44 power supply
45 timing unit
46 interface unit
50 adjustment unit
51 pump
52 valve
53 pump drive circuit
54 valve drive circuit
70A, 70B artery volume sensor
71A, 71B light emitting element
72A, 72B light receiving element
73A, 73B light emitting element drive circuit
74A, 74B artery volume detection circuit
76A, 76B artery volume detection unit measurement data
100 CPU
102 cuff pressure acquiring unit
104 detection processing unit
106 measurement control unit
108 servo control unit
110 blood pressure determining unit
112, 112A congestion detection unit
114 specification processing unit
114A stop processing portion
114B notification processing portion
114C recording processing portion
132 recording medium
302 wrist
304 finger base portion
306 finger tip portion
F_PPGdc artery volume signal of peripheral site after filtering
MPGac artery volume change signal of measurement site
MPGdc artery volume signal of measurement site
PC cuff pressure
PC0 initial cuff pressure
PPGac artery volume change signal of peripheral site
PPGdc artery volume signal of peripheral site
V0 control target value

The invention claimed is:

1. A blood pressure information measurement device for measuring blood pressure information according to a volume compensation method, the blood pressure information measurement device comprising:
a cuff to be wrapped around a predetermined measurement site;
a pressure detection unit that detects a cuff pressure representing a pressure in the cuff;
a first volume detection unit, arranged at a predetermined position of the cuff, that detects a volume of a first artery at the measurement site;
a second volume detection unit that detects a volume of a second artery at a peripheral site, which is a site on a peripheral side than the measurement site;
a detection processing unit that performs a process for detecting a target value of a servo control;
a servo control unit that carries out the servo control so that a difference between the volume of the first artery and the target value of the servo control is smaller than or equal to a predetermined value;

a blood pressure determination unit that determines the cuff pressure when an amplitude in change in volume of the first artery is smaller than or equal to the predetermined value as a blood pressure according to the servo control; and a congestion detection unit that detects congestion of the peripheral site based on an output from the second volume detection unit during a period of servo control.

2. The blood pressure information measurement device according to claim 1, wherein the congestion detection unit detects congestion by detecting a temporal change for the volume of the second artery from a beginning of a measurement.

3. The blood pressure information measurement device according to claim 2, wherein the congestion detection unit detects congestion from a ratio or a difference of a current amount of change in the volume of the second artery and an amount of change in the volume of the second artery at the beginning of a measurement.

4. The blood pressure information measurement device according to claim 2, wherein the congestion detection unit detects congestion from a ratio or a difference of a current volume value of the second artery and a volume value of the second artery at the beginning of a measurement.

5. The blood pressure information measurement device according to claim 2, wherein the beginning of the measurement represents a time point at which the amplitude in the change in volume of the first artery becomes smaller than or equal to the predetermined value for a first time since the servo control started.

6. The blood pressure information measurement device according to claim 2, wherein the beginning of the measurement represents a time point at which the target value of the servo control is detected.

7. The blood pressure information measurement device according to claim 2, wherein the beginning of the measurement represents a time point before a start of the process of the detection processing unit.

8. The blood pressure information measurement device according to claim 1, further comprising:

a stop processing unit that performs a process of stopping the measurement when congestion is detected by the congestion detection unit.

9. The blood pressure information measurement device according to claim 1, further comprising:

a notification processing unit that performs a process of notifying congestion information when congestion is detected by the congestion detection unit.

10. The blood pressure information measurement device according to claim 9, wherein the notification processing unit notifies the detection of the congestion as the congestion information.

11. The blood pressure information measurement device according to claim 9, wherein the congestion detection unit further determines a congestion level, and wherein the notification processing unit notifies the congestion level as the congestion information.

12. The blood pressure information measurement device according to claim 1, further comprising:

a storage unit that stores the blood pressure information corresponding to a determination result by the blood pressure determination unit; and a recording processing unit that performs a process of recording presence of detection of congestion by the congestion detection unit in the storage unit in association with the blood pressure information.

* * * * *